United States Patent [19]

Ekwall

[11] Patent Number: 5,193,538
[45] Date of Patent: Mar. 16, 1993

[54] IN VIVO IMPLANTABLE MEDICAL DEVICE WITH BATTERY MONITORING CIRCUITRY

[75] Inventor: Christer Ekwall, Spånga, Sweden

[73] Assignee: Siemens Aktiengesellschaft, Munich, Fed. Rep. of Germany

[21] Appl. No.: 743,391

[22] PCT Filed: Feb. 14, 1990

[86] PCT No.: PCT/FP90/00239
§ 371 Date: Jan. 9, 1992
§ 102(e) Date: Jan. 9, 1992

[87] PCT Pub. No.: WO90/09208
PCT Pub. Date: Aug. 23, 1990

[30] Foreign Application Priority Data

Feb. 14, 1989 [SE] Sweden .............................. 8900490-7
Feb. 14, 1989 [SE] Sweden .............................. 8900491-5
Feb. 14, 1989 [SE] Sweden .............................. 8900492-3
Feb. 14, 1989 [SE] Sweden .............................. 8900493-1

[51] Int. Cl.⁵ ............................................ A61N 1/378
[52] U.S. Cl. ...................... 128/419 PT; 128/419 PG; 128/419 PS
[58] Field of Search .................. 128/419 PG, 419 PT, 128/419 PS

[56] References Cited
U.S. PATENT DOCUMENTS

| 4,120,306 | 10/1978 | Renirie . |
| 4,290,429 | 9/1981 | Blaser . |
| 4,324,251 | 4/1982 | Mann ............................. 128/419 PT |
| 4,390,020 | 6/1983 | Herpers . |
| 4,416,282 | 11/1983 | Saulson et al. . |
| 4,481,950 | 11/1984 | Duggan . |
| 4,485,818 | 12/1984 | Leckrone et al. . |
| 4,606,350 | 8/1986 | Frost . |
| 4,715,381 | 12/1987 | Moberg ........................ 128/419 PT |

FOREIGN PATENT DOCUMENTS
0160801 11/1985 European Pat. Off. .

Primary Examiner—Kyle L. Howell
Assistant Examiner—Kennedy J. Schaetzle
Attorney, Agent, or Firm—Hill, Steadman & Simpson

[57] ABSTRACT

It is known that modern implantable electromedical devices for the stimulation of a physiological function, such as pacemakers, are programmable to work in different stimulating modes and comprise sensing and evaluating means for monitoring the capacity of the battery within the device. In order to achieve a constant time duration between the point in time when the battery capacity drops below a threshold value and the end of life of the battery, said threshold value is varied in dependence on the utilized stimulating mode in such a way that a higher threshold value is selected for a stimulating mode with a high energy consumption and vice versa.

13 Claims, 2 Drawing Sheets

IN VIVO IMPLANTABLE MEDICAL DEVICE WITH BATTERY MONITORING CIRCUITRY

BACKGROUND OF THE INVENTION

In a living body implantable electromedical device The present invention relates to an electromedical device implantable in a living body and comprising stimulating means for the stimulation of a physiological function in the living body, stimulating mode selector means connected to said stimulating means to enable modification of said stimulation by selecting one or more out of a plurality of available&imulating modes, a power source in the form of a battery for powering said stimulating means and stimulating mode selector means, sensing means connected to said battery to enable sensing of the instantaneous battery capacity and evaluating means connected to said sensing means to establish whether said battery capacity, on a sensing event, is higher or lower than a predetermined first threshold value adapted to guarantee, in an assumed standard operation of the device, its function within a predetermined time interval during which said battery capacity shall exceed a lower second threshold value.

The invention is primarily intended for use with an electromedical device such as a pacemaker, which is intended to stimulate the cardiac function of the living body by means of generated electrical pulses different in time when said cardiac function deviates from normal.

A device of the type initially cited is disclosed by U.S. Pat. No. 390 020. This device relates to a programmable pacemaker capable of operating in several stimulating modes, having battery powered stimulating means and stimulating mode selector means. Sensing and evaluating means, which can be activated externally by means of a magnet, for example at a medical examination, monitor the terminal voltage of the battery and cause the pacemaker via the stimulating selector means to change operation from a first stimulating mode with a programmed stimulation rate to said mode with a fixed stimulation rate, when the terminal voltage decreases below a first threshold value, and to operate in a second predetermined stimulating mode at a fixed stimulation rate when the terminal voltage decreases below the first and a lower second threshold value. The limitation to a predetermined stimulating mode at a fixed rate decreases the current demand from the battery and indicates to the patient or an observing physician that the pacemaker should be replaced.

U.S. Pat. No. 4,416,282 discloses a similar pacemaker, which also includes sensing and evaluating means for monitoring of the battery capacity with regard to two battery depletion levels. The stimulation rate automatically decreases with the decreasing of the battery capacity below the depletion levels.

As is known from U.S. Pat. No. 4,606,350 or U.S. Pat. No. 4,290,429, the battery monitoring can be performed by cutting off all current flow from the battery to the pacemaker circuitry, which, however, is still powered by a by-pass capacitor, whereby a test capacitor is connected to the battery and the time period needed for the voltage across the test capacitor to reach a predetermined value gives a measure of the internal resistance of the battery.

From U.S. Pat. No. 4,481,950, another method to monitor the battery capacity is known, where the battery is loaded with a predetermined load and the battery terminal voltage is sensed. The sensed voltage gives a measure of the internal resistance of the battery, the value of which has a certain unambiguous relation to the instantantaneous battery capacity. As is known from U.S. Pat. No. 4,120,306, the internal resistance value of lithium-type batteries usually used for pacemakers is lower, the higher the battery capacity and vice versa.

When the monitoring of the battery capacity is activated as described in connection with the above mentioned U.S. Pat. No. 4,390,020, the battery capacity must be sufficiently high to guarantee operation of the pacemaker under definite conditions during a predetermined time interval up to the next medical examination; otherwise the approaching of the end of life (EOL) of the battery must be indicated, so that the physician can take necessary action in order to replace the pacemaker. As some time may pass between the sensing of low battery capacity and the point in time when the pacemaker can be replaced, a date for replacement of the pacemaker by a physician must be carefully selected. From this point in time, hereafter called elective replacement time (ERT), when the battery capacity approaches a critical first threshold value (ERT-value) till the end of life (EOL) of the battery, when the battery capacity approaches a lower second threshold value (EOL-value), the function of the pacemaker under given conditions, i.e., in an assumed standard operation, must be guaranteed. It is not unusual to have the time period between ERT and EOL, also called "safety time", set longer than three months, whereby the EOL-value can be set so low that the pacemaker ceases to function when it reaches this value or set: somewhat above this value, in which case it may be suitable to provide an alarm function.

Modern pacemakers of the type mentioned at the beginning are, however, made programmable in order to adjust stimulating mode, including other parameters such as output energy, to different physiological needs. The energy consumption of the device is hereby changed. Therefore, not only the time period from the beginning of life of the battery up to the point in time of reaching the ERT-value but also the safety time will be shorter for stimulating modes with a high energy consumption and/or at a high degree of utilization and vice versa.

Thus it appears as a technical problem that, due to a changed stimulating mode, an estimate of the EOL is no longer accurate or valid, so that during the safety time, the function of the device cannot be guaranteed. It is to be noted that even temporary drops of the battery voltage below a minimum voltage supply level are fatal; memory or parameter loss may be the result. It is an object of the present summary of the invention to achieve a constant safety time between the appearance of the ERT-value and the EOL-value.

In accordance with the invention, this object is achieved in that the sensing and evaluating means of the device specified at the beginning are arranged to vary the first threshold value (ERT-value) in dependence on the utilized stimulating mode and in dependence on the degree of utilization of previously selected stimulating modes recorded in and available from the stimulating mode selector means in such a way that a higher threshold value is selected for stimulating modes with a higher energy consumption and higher degree of utilization and a lower threshold value is selected for stimulating modes with a lower energy consumption and lower degree of utilization.

Thus, an adaptation and stabilization of the time duration between the appearing of the ERT-value and the point in time of the EOL-value is achieved according to the utilized stimulating mode, which deviates from an assumed standard stimulating mode. Thus the required safety time is always present.

According to a first embodiment of the invention, it is suggested that, on the sensing event, the battery is loaded with a standard load or a standard current, which corresponds to the load or device current consumption during the standard operation, and that the terminal voltage of the battery is compared to a reference voltage representing said first threshold value and being adjustable in dependence on the device energy consumption in the utilized stimulating mode.

The comparison can be carried out by a voltage comparator which compares the terminal voltage of the battery with said reference voltage which is generated by a digital-to-analog converter; this digital-to-analog converter is controlled by a counter which is adjustable by the stimulating selector means to a value corresponding to said first threshold value.

According to another embodiment of the invention, the battery is loaded with an adjustable load or current representing said first threshold value and corresponding to the energy consumption of the selected stimulating mode. In this case, the terminal voltage of the battery is compared with a fixed reference voltage.

The adjustable load can be made up of a number of fixed loads which are connectable to the battery, separately or together.

A further step to keep the safety time constant is, when the ERT-value appears, to limit the selection of the stimulating modes to those with a reduced energy consumption. This limitation can be adapted to the current depletion of the battery by increasing the number of stimulating modes to be inhibited for selection over a period of time. The limitation itself can also be inhibited during a predetermined delay time when a low degree of utilization of the previously selected stimulating mode is established.

An adaptation of the limitation to the current battery depletion can also be achieved by repetition of the battery test after a predetermined time duration following the appearing of the ERT-value. The battery capacity is now compared with a third threshold value between said first and second threshold values, and an additional limitation of stimulating modes is implemented when the now sensed battery capacity is below said third threshold value.

DESCRIPTION OF THE DRAWINGS

A preferred embodiment of the implantable electromedical device according to this invention will now be described in greater detail with reference to the attached drawings. In the drawings.

DESCRIPTION OF THE PREFERRED EMBODIMENTS

Figure 1:
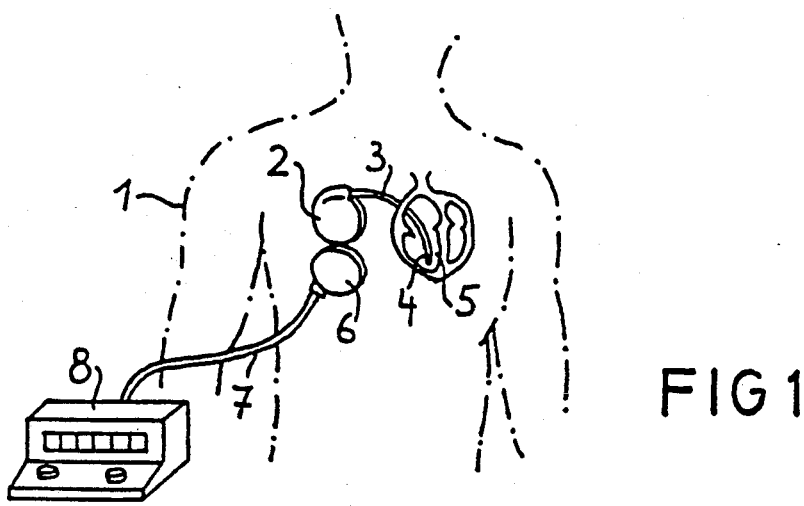
FIG. 1 shows said implantable electromedical device in the form of a pacemaker, where a desired stimulating mode is programmable into the pacemaker by way of an external terminal.

Referring to FIG. 1, an electromedical device 2 in the form of a pacemaker implantable in a living body (patient) 1 is shown, which pacemaker 2 is connected via an electrode lead 3 to an electrode 4 for tissue stimulation. The electrode 4 is placed within a ventricle 5 of the patient's 1 heart. By means of an external telemetry head 6 connected to a terminal 8 via a flexible cable 7, the pacemaker 2 can be adjusted to act either in a standard stimulating mode or in one or more out of a plurality of available stimulating modes.

The following description is based on the fact that each stimulating mode requires an energy consumption deviating from other stimulating modes when activated. The real energy consumption will therefore be dependent on both the selected mode and its degree of utilization.

Moreover, the pacemaker 2 is provided with such circuits that no set stimulating mode is activated at normal cardiac activity, as each pulse for cardiac contraction is constantly inhibited by the rhythm of sensed activity of the cardiac muscle. For this, a slight consumption of energy is required. At enduring abnormal cardiac activity, a continuous activation of a stimulating mode and its pulse accompanied by a corresponding high energy consumption is required.

As the selection of different stimulating modes, their activation in case of missing inhibiting signals and other parts and functions are previously known, and are not important for the understanding of this invention, they will not be described in further detail.

Figure 2:
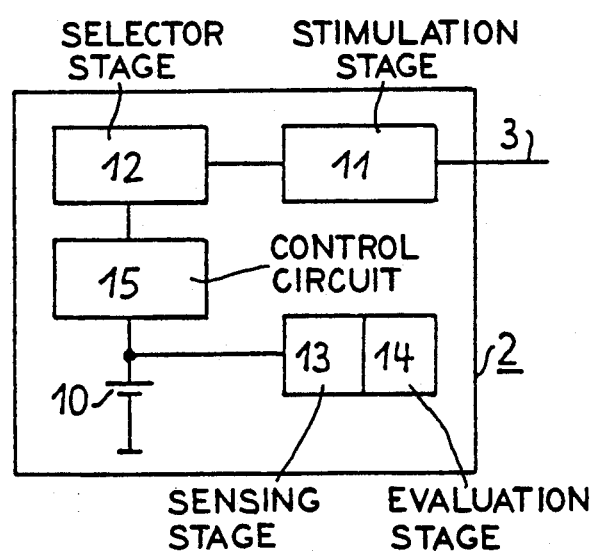
FIG. 2 is a schematic block diagram showing the substantial parts of the pacemaker.
Figure 2:
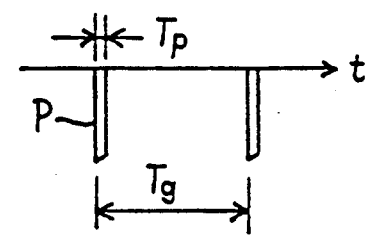

However, with reference to FIG. 2, some parts of the pacemaker 2 are shown greatly simplified in the form of a block diagram. The pacemaker 2 comprises stimulating means 11 connected at its output to the electrode lead 3 to enable stimulation of the patient's 1 heart by means of a rush of current or pulse P with a duration Tp and a pulse repetition time Tg. The pacemaker 2 further comprises a stimulating mode selector means 12 connected to the stimulating means 11 to enable modification of the stimulation by selecting one out of a plurality of available stimulating modes. This stimulating mode selector means 12, which can be adaptively or externally actuated, is controlled by a memory and control circuit 15 for controlling amplitude, frequency and duration of the stimulating pulses. The pacemaker 2 is powered by an internal power source 10 in form of a lithium-iodide battery. The battery 10 is further connected to a sensing means 13 and a following evaluating means 14 to enable sensing of remaining or instantaneous battery capacity and to establish whether said battery capacity, on a sensing event, is higher or lower than a predetermined first threshold value. This threshold value or ERT-value is adjusted to guarantee, in an assumed standard or normal operation of the pacemaker 2, a continuous normal function of the same up to a point in time, when the battery capacity exceeds a lower second threshold value or EOL-value, which represents the end of life of the battery 10. The time period during which the battery capacity has values between the first and second threshold value will hereafter be designated "safety time".

Figure 3:
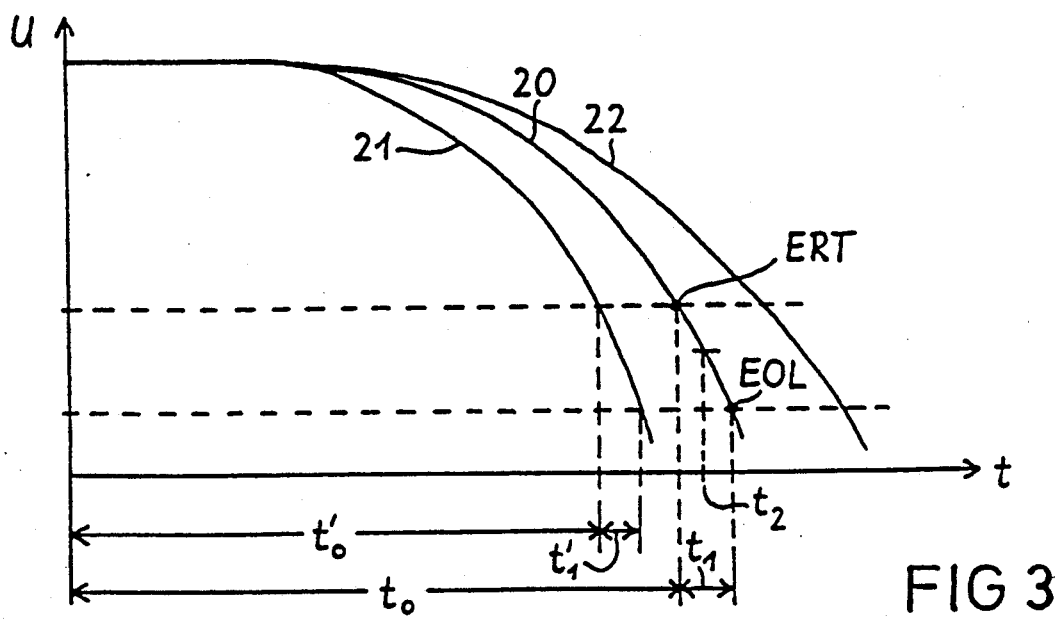
FIG. 3 is a time diagram valid for a battery used in the pacemaker and showing the battery capacity as a function of time during the life of the battery.

FIG. 3 refers to a time diagram valid for the battery 10 and significative of the battery capacity during the life time of the battery 10. As it is known that the battery capacity of a lithium-iodide battery is connected with its internal resistance and that the internal resistance can be measured by sensing the terminal voltage of the battery 10 at a known load, the battery capacity is represented as the terminal voltage U. The graph 20 shows the terminal voltage of the battery 10 when the battery 10 is loaded with an assumed standard load or at a corresponding standard current. This graph 20 is therefore also valid for the selection of one or more stimulating modes with an equal current consumption. As shown, the battery capacity decreases with time and exceeds the first threshold value (ERT-value) after approximately 7.5 years. Within the safety time $t_1$ (approximately 8 months) following the ERT value, the battery capacity drops below the second threshold value EOL. The first threshold value or ERT value is adjusted to guarantee, in the standard or normal operation of the pacemaker 2, a continuous function of the same during the safety time $t_1$. This means that at no point in time during the safety time $t_1$, the terminal voltage drops below a minimum voltage, which is represented by the ECL-value, and is necessary for the function of the pacemaker 2.

As shown by graph 21, the battery capacity decreases faster by loading the battery 10 with a current higher than the standard current. Thus, with a higher energy consumption according to graph 21, not only the time duration $t'_0$—from the beginning of life of battery 10 till the battery capacity falls below the ERT-value—but also the safety time $t'_1$ will be somewhat shorter than the time duration $t_0$ and the safety time $t_1$, respectively, at standard operation. In contrast to this, the safety time will be longer than $t_1$ with a lower energy consumption according to graph 22.

It is, however, important to achieve a safety time equally long regardless of whether the selected stimulating mode requires the standard energy consumption or any other higher or lower energy consumption. The reason for this is that it is desirable to keep the time duration $t_0$, within which any operating mode of the pacemaker 2 is possible, as long as possible, but also to guarantee a safety time $t_1$ long enough. It is thus important to note that when the battery capacity drops below the ERT-value in an assumed operating mode, there is an imminent risk of selecting another stimulating mode which requires an energy consumption lowering the terminal voltage of the battery 10 below the minimum value required for the function of the pacemaker 2. During the safety time, it is therefore suitable to introduce a restriction in the selection of stimulating modes so that there is only a selection of stimulating modes having an energy consumption lower than a predetermined value.

It should be further noted that when the battery capacity is below the ERT-value, the terminal voltage must not be lower than the current voltage valid for the EOL-value of the selected stimulating mode. So, the safety time must be selected in consideration of the possibility that the degree of utilization of the selected stimulating mode could increase drastically. Therefore, for an expected maximum degree of utilization, an ERT-value higher than for a somewhat reduced degree has to be chosen, so that the pacemaker 2 is able to function with a 100% degree of utilization, or at least 80%, during the safety time.

Furthermore, the selected ERT-value is dependent on the length of the determined safety time with a higher value for a longer safety time than for a shorter one.

Figure 4:
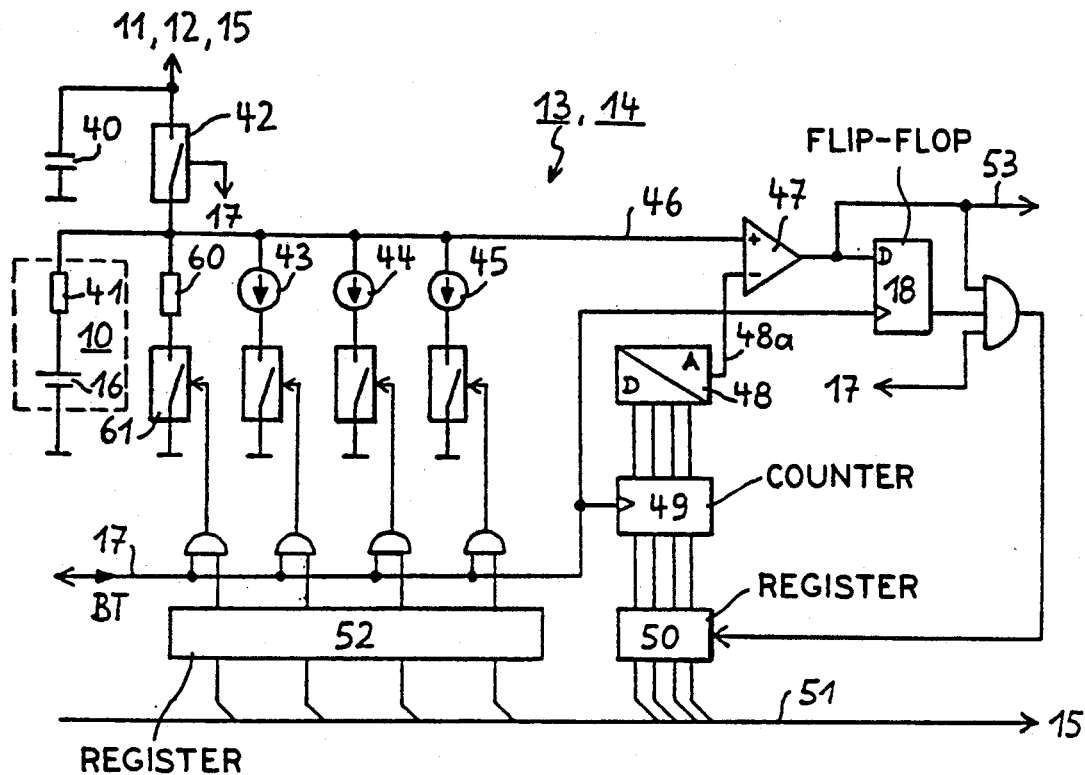
FIG. 4 is a more detailed circuit diagram sensing and evaluating means shown in FIG. 2.

Referring now to FIG. 4, a more detailed circuit diagram of the sensing and evaluating means 13, 14 is shown. The battery 10 is represented by an ideal voltage source 16 connected in series to an internal resistance 41, the resistance value of which increases with decreasing battery capacity. The battery 10 is tested when a signal BT is applied to line 17. In the sensing event on the signal BT, the battery 10 is disconnected from the memory and control circuit 15 by a switch 42; the circuit 15, however, is still powered by a charged by-pass capacitor 40.

During the test, the battery 10 is loaded by a standard load 60 or, alternatively, by a standard current generator connected to the battery 10 by a switch 61. The battery terminal voltage, the values of which comply with graph 20 in FIG. 3 and gives a measure of the remaining battery capacity, is sensed on the line 46. By means of a voltage comparator 47, the sensed voltage on the line 46 is compared to an adjustable reference voltage on the output line 48a of a digital-to-analog converter (D/A-converter) 48, which is controlled by a counter 49. This counter 49 is adjustable by the stimulating mode selector means 12 (FIG. 1) via a data bus 51 and a register 50 to an ERT-value corresponding to the selected stimulating mode, whereby, for a stimulating mode with a high energy consumption, the ERT-value is higher than for a stimulating mode with a lower energy consumption. It is further possible to take corrections for certain stimulating parameters to increase the ERT-value when a high degree of utilization of the selected stimulating mode is established and vice versa and to adjust the position of the counter 49 to a value, for a desired long safety time, higher than the value for a shorter safety time. No activation takes place at battery tests when the terminal voltage of the battery 10 exceeds the reference voltage on line 48a. If, however, the terminal voltage on line 46 agrees with or is lower than the reference voltage, the voltage comparator 47 changes its output state and starts the safety time via the output line 53.

The circuit diagram of the sensing and evaluating means shown in FIG. 4 also offers another possibility to adapt the ERT-value to the selected stimulating mode. In this case, a number of current sources 43, 44 and 45, or, alternatively, different loads, can be set separately or together with or without the standard load 60 according to the energy consumption of the selected stimulating mode. The amount of the test load, i.e., the load during battery test, is controlled by a register 52. This register 52 is set via the data bus 51 by the stimulating mode selector means 12 as described above for register 50.

The voltage on the line 46 is now compared to a fixed reference voltage on the line 48a corresponding to a predetermined value in the counter 49. This predetermined value may be the ERT-value selected for the operation of the pacemaker 2 in the standard stimulating mode.

No activation takes place at battery tests when the terminal voltage of the battery 10 exceeds the reference voltage on line 48a. If, however, the terminal voltage on line 46 agrees with or is lower than the reference voltage, the voltage comparator 47 changes its output state and starts the safety time.

It is further possible to measure the current battery capacity or terminal voltage at a medical examination, whereby several successive signals BT are applied to the line 17. At each signal BT, the terminal voltage of the battery 10 is compared to a reference voltage on the line 48a. After every performed signal BT, the counter 49 is incremented (or decremented) one step as is also the reference voltage. When the reference voltage reaches the value of the terminal voltage, the voltage comparator 48 changes its output state. This generates, by means of a flip-flop 18, a signal for copying the content of the counter 49 to the register 50. This value now stored in register 50 corresponds to the battery capacity and can be called off via data bus 51 for transmission to the terminal (FIG. 1).

Figure 5:
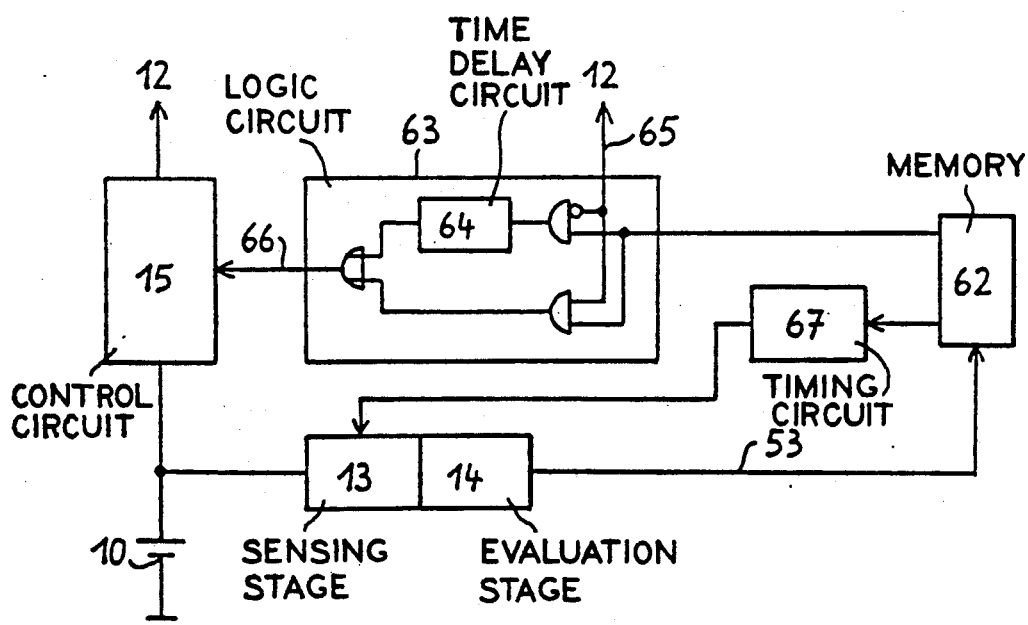
FIG. 5 a schematic drawing of means for reducing the selection of stimulating modes if the battery capacity drops below a predetermined value.

As FIG. 5 shows, the output line 53 of the sensing and evaluating means 13, 14 is connected to a memory 62, for example a flip-flop, which stores the output state of the comparator 47 shown in FIG. 4. When the appearance of the ERT-value is detected and the corresponding output state of the comparator 47 is stored, the memory 62 delivers a signal to a logic circuit 63 containing a time delay circuit 64. The logical circuit 63 receives, from the stimulating mode selector means 12 via line 65, a signal indicating whether the degree of utilization of previously selected stimulating modes is high or low. At a high degree of utilization, the logic circuit 63 generates a limitation signal supplied via line 66 to the memory and control circuit 15 for limitation of the selection of the stimulating modes to those with a reduced energy consumption. The number of stimulating modes to be inhibited for selection can be automatically increased with time. If the signal on the line 65 indicates a low degree of utilization of the previously selected stimulating modes, the time delay circuit 64 is started to inhibit the limitation of stimulating modes during a predetermined delay time.

After the appearance of the ERT-value, the memory 62 starts, simultaneously with the activation of the logical circuit 63, a timing circuit 67, which, after a predetermined time duration at a moment $t_2$ (FIG. 3), activates the sensing and evaluating means 13, 14 for a further sensing of the battery capacity to establish whether the battery capacity at the moment $t_2$ is higher or lower than a predetermined third threshold value between the first and second threshold value. The time duration is selected in such a way that the moment $t_2$ occurs between the appearance of the ERT-value and the EOL-value, for example after the expiration of half of the safety time $t_1$. If the sensed battery capacity at the moment $t_2$ is below said third threshold value, an additional limitation of the selection of the stimulating modes to those with a more reduced energy consumption is implemented in the way described above in connection with the appearance of the ERT-value. At the same time, the patient can be reminded to see a physician for the replacement of the pacemaker.

Although modifications and changes may be suggested by those skilled in the art, it is the intention of the inventor to embody within the patient warranted hereon all changes and modifications as reasonably and properly come within the scope of his contribution to the art.

I claim:

1. An electromedical device comprising:
   stimulation means, adapted for in vivo implantation in a patient for stimulating a physiological function in said patient,
   mode selector means, connected to said stimulation means, for selecting one mode of stimulating said physiological function from a plurality of available stimulation modes;
   memory means connected to said mode selector means for recording the number of times each stimulation mode is selected;
   a battery connected by supplying power to said stimulation means and to said mode selector means, each of sid available stimulation modes having an energy consumption from said battery associated therewith;
   sensing means connected to said battery for measuring an instantaneous battery capacity;
   evaluation means, connected to said sensing measn, for determining whether said instantaneous battery capacity, as measured by said sensing measn, is above or below a predetermined first threshold value selected to insure standard operation of said stimulation means within a predetermined time interval during which said battery capacity shall exceed a second threshold value, said second threshold value being lower than said first threshold value; and
   means for varying said first threshold value, dependent on which of said stimulation modes is currently selected, based on the energy consumption and number of times selected of the currently selected stimulation mode, by setting a higher first threshold value for a currently selected stimulation mode having a higher energy consumption and a higher number of times selected and setting a lower threshold value for a currently selected stimulation mode having a lower energy consumption and a lower number of times selected.

2. An electromedical device as claimed in claim 1 further comprising:
   means for loading said battery, during sensing of said instantaneous battery capacity by said sensing means, with a standard load corresponding to a load during said standard load corresponding to a load during said standard operation; and
   wherein said means for varying includes a comparator having a first input to which the terminal voltage of said battery is supplied, and a reference voltage input supplied with a voltage representing said first threshold value, and means for adjusting said reference voltage dependent on the energy consumption from said battery during said currently selected stimulation mode, said comparator generating an output signal indicating whether said instantaneous battery capacity is higher or lower than said reference voltage.

3. An electromedical device as claimed in claim 2 wherein said means by adjusting said reference voltage is a counter which counts to a count determined by said mode selector means corresponding to said first threshold value, and a digital-to-analog converter connected to an output of said counter for generating a voltage, as said reference voltage, corresponding to said count.

4. An electromedical device as claimed in claim 1 further comprising:
   means for loading said battery, during sensing of said instantaneous battery capacity by said sensing means, with a standard current consumption corresponding to a current during said standard operation; and wherein said means for varying includes a comparator having a first input to which the terminal voltage of said battery is supplied, and a reference voltage input supplied with a voltage representing said first threshold value, and means for adjusting said reference voltage dependent on the energy consumption from said battery during said currently selected stimulation mode, said comparator generating an output signal indicating whether said instantaneous battery capacity is higher or lower than said reference voltage.

5. An electromedical device as claimed in claim 4 wherein said means for adjusting said reference voltage is a counter which counts to a count determined by said mode selector means corresponding to said first threshold value, and a digital-to-analog converter connected to an output of said counter for generating a voltage, as said reference voltage, corresponding to said count.

6. An electromedical device as claimed in claim 1 further comprising:
   means for loading said battery, during sensing of si instantaneous battery capacity by said sensing means, with an adjustable load which causes the generation of a voltage used as used first threshold value;
   means for adjusting said adjustable load so that said first threshold value corresponds to a load representative of said currently selected stimulation mode; and
   a comparator having a first input supplied with a terminal voltage of said battery and a second input to which said reference voltage is supplied, said comparator generating an output signal indicating whether said instantaneous battery capacity is higher or lower than said first threshold value.

7. An electromedical device as claimed in claim 6 wherein said adjustable load consists of a plurality of separate loads, and wherein said means for adjusting is a means for selecting a combination of said separate loads which generates a voltage corresponding to said first threshold value.

8. An electromedical device as claimed in claim 1 further comprising:
   means for loading said battery, during sensing of sid instantaneous battery capacity by said sensing measn, with an adjustable current source which causes the generation of a voltage used as said first threshold value;
   means for adjusting said adjustable current source so that sid first threshold value corresponds to a current consumption representative of said currently selected stimulation mode; and
   a comparator having a first input supplied with a terminal voltage of said battery and a second input to which said reference voltage is supplied, said comparator generating an output signal indicating whether said instantaneous battery capacity is higher or lower than said first threshold value.

9. An electromedical device as claimed in claim 1 wherein said evaluation measn includes means for generating a limitation signal supplied to said mode selector means for limiting the selection among said available stimulation modes to stimulation modes having a lower energy consumption.

10. An electromedical device as claimed in claim 9 further comprising means for decreasing over time the number of stimulation modes to which selection by said mode selection means is limited.

11. An electromedical device as claimed in claim 9 further comprising:
    time delay means for inhibiting the limitation of said stimulating modes for a predetermined delay time; and
    means for enabling said time delay means when a selected stimulation mode has a low number of times it has been selected.

12. An electromedical device as claimed in claim 1 further comprising timing means, connected to said sensing means and said evaluation means, which is enabled by said evaluation means when the instantaneous battery capacity reaches said first threshold value for, after a predetermined time duration, activating said sensing means for making a further measurement of said instantaneous battery capacity; and
    means for determining whether said further measurement of said instantaneous battery capacity is higher or lower than a predetermined third threshold value between said first and second threshold values.

13. An electromedical device as claimed in claim 12 further comprising:
    means for limiting the selection of said available stimulation modes to stimulation modes having a lower energy consumption when said further measurement of said instantaneous battery capacity at said predetermined time is below said third threshold value.

* * * * *